United States Patent
Takata et al.

(10) Patent No.: US 11,485,717 B2
(45) Date of Patent: Nov. 1, 2022

(54) METHOD FOR PRODUCING EPOXY COMPOUND

(71) Applicant: ENEOS CORPORATION, Tokyo (JP)

(72) Inventors: Shohei Takata, Tokyo (JP); Kenta Ue, Tokyo (JP); Takeshi Koike, Tokyo (JP); Atsushi Kameyama, Tokyo (JP)

(73) Assignee: ENEOS CORPORATION, Tokyo (JP)

( * ) Notice: Subject to any disclaimer, the term of this patent is extended or adjusted under 35 U.S.C. 154(b) by 0 days.

(21) Appl. No.: 17/274,123

(22) PCT Filed: Aug. 19, 2019

(86) PCT No.: PCT/JP2019/032325
§ 371 (c)(1),
(2) Date: Mar. 5, 2021

(87) PCT Pub. No.: WO2020/049991
PCT Pub. Date: Mar. 12, 2020

(65) Prior Publication Data
US 2021/0340118 A1    Nov. 4, 2021

(30) Foreign Application Priority Data
Sep. 7, 2018   (JP) .............................. JP2018-168149

(51) Int. Cl.
*C07D 301/12*   (2006.01)
*B01J 23/30*    (2006.01)
*B01J 27/055*   (2006.01)
*B01J 31/02*    (2006.01)
*C07D 407/04*   (2006.01)
*C07D 493/04*   (2006.01)

(52) U.S. Cl.
CPC ............ *C07D 301/12* (2013.01); *B01J 23/30* (2013.01); *B01J 27/055* (2013.01); *B01J 31/0239* (2013.01); *B01J 31/0259* (2013.01); *C07D 407/04* (2013.01); *C07D 493/04* (2013.01); *B01J 2231/72* (2013.01)

(58) Field of Classification Search
CPC .. C07D 301/12; C07D 407/04; C07D 493/04; C07D 303/04; C07D 303/06; C07D 493/08; C07D 303/22; B01J 23/30; B01J 27/055; B01J 31/0239; B01J 31/0259; B01J 2231/72; B01J 31/0268; C07B 61/00
USPC ........................................................ 549/531
See application file for complete search history.

(56) References Cited

U.S. PATENT DOCUMENTS

2015/0018515 A1   1/2015  Hosokawa et al.
2016/0347763 A1  12/2016  Ichihara et al.
2017/0204077 A1   7/2017  Hosokawa et al.

FOREIGN PATENT DOCUMENTS

| JP | S49-126658 A | 12/1974 |
|----|--------------|---------|
| JP | 2012-025688 A | 2/2012 |
| JP | 2015-091788 A | 5/2015 |
| JP | 2015-166335 A | 9/2015 |
| JP | 2016-204364 A | 12/2016 |
| WO | 2013/147092 A1 | 10/2013 |
| WO | 2015/076222 A1 | 5/2015 |

OTHER PUBLICATIONS

KANG et al., "Improvement of the Phase-Transfer Catalysis Method for Synthesis of Glycidyl Ether," *J. Am. Oil Chem. Soc.*, 78(4): 423-429 (2001).
Vasylyev et al., "New Heterogeneous Polyoxometalate Based Mesoporous Catalysts for Hydrogen Peroxide Mediated Oxidation Reactions," *J. Am. Chem. Soc.*, 126(3): 884-890 (2004).
Zhang et al., "The epoxidation of olefins catalyzed by a new heterogeneous polyoxometalate-based catalyst with hydrogen peroxide," *Catalysis Communications*, 12(4): 318-322 (2010).
Japanese Patent Office, International Search Report in International Patent Application No. PCT/JP2019/032325 (dated Oct. 15, 2019).
Japanese Patent Office, International Preliminary Report on Patentability in International Patent Application No. PCT/JP2019/032325 (dated Mar. 9, 2021).
European Patent Office, Extended European Search Report in European Patent Application No. 19857674.6 (dated Apr. 8, 2022).

*Primary Examiner* — Taylor V Oh
(74) *Attorney, Agent, or Firm* — Leydig, Voit & Mayer, Ltd.

(57) ABSTRACT

The invention provides a method for producing an epoxy compound by hydrogen peroxide using an organic compound having a carbon-carbon double bond as a raw material, wherein a by-product is suppressed from being generated and the epoxy compound is produced in a high yield. In particular, the invention provides a method for producing an epoxy compound involving oxidizing a carbon-carbon double bond in an organic compound with hydrogen peroxide in the presence of a catalyst, wherein the catalyst comprises a tungsten compound; a phosphoric acid, a phosphonic acid or salts thereof; and an onium salt having an alkyl sulfate ion represented by formula (I) as an anion:

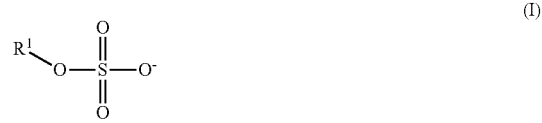

(I)

wherein $R^1$ is a linear or branched aliphatic hydrocarbon group having 1 to 18 carbons, which may be substituted with 1 to 3 phenyl groups.

20 Claims, No Drawings

METHOD FOR PRODUCING EPOXY COMPOUND

CROSS-REFERENCE TO RELATED APPLICATIONS

This patent application is the U.S. national phase of International Patent Application No. PCT/JP2019/032325, filed Aug. 19, 2019, which claims the benefit of Japanese Patent Application No. 2018-168149, filed Sep. 7, 2018, both of which are incorporated herein by reference in their entireties.

FIELD OF THE INVENTION

The present invention relates to a method for producing an epoxy compound.

BACKGROUND ART

As a conventional method for producing an epoxy compound, a method is known in which, for example, olefins are oxidized with peracids such as peracetic acid (Patent Document 1). However, there are problems that (i) peracids require caution in handling, (ii) an epoxy compound produced reacts with a carboxylic acid present in the reaction system to produce an ester, which lowers the selectivity of the epoxy compound, (iii) a coexisting organic acid easily reacts with an epoxy group generated in the presence of water in the production of an alicyclic epoxy compound having high reactivity with acid, and the ring of the epoxy group opens, which lowers the selectivity of the epoxy compound, (iv) post-treatment after the reaction is troublesome, etc.

As described above, none of the conventional methods for epoxidizing an organic compound having a carbon-carbon double bond is deemed to be industrially advantageous from the viewpoint of safety and efficiency.

PRIOR ART DOCUMENTS

Patent Literature

Patent Document 1: 3PS49-126658

SUMMARY OF THE INVENTION

Problems to be Solved by the Invention

Provided is a method for producing an epoxy compound by hydrogen peroxide using an organic compound having a carbon-carbon double bond as a raw material, wherein a by-product is suppressed from being generated and the epoxy compound is produced in a high yield.

As a result of diligent study of the method for producing an epoxy compound in a high yield, the present inventors have found that an epoxy compound can be efficiently produced by using an onium salt with a specific anion as a phase transfer catalyst. The present invention Is based on these findings.

Means for Solving Problems

That is, the present invention encompasses the following inventions.

[1] A method for producing an epoxy compound, comprising a step of oxidizing a carbon-carbon double bond in an organic compound with hydrogen peroxide in the presence of a catalyst, wherein the catalyst comprises a tungsten compound; a phosphoric acid, a phosphonic acid or salts thereof; and an onium salt having an alkyl sulfate ion represented by formula (I) as an anion:

wherein $R^1$ is a linear or branched aliphatic hydrocarbon group having 1 to 18 carbons, which may be substituted with 1 to 3 phenyl groups.

[2] The production method according to [1], wherein the onium salt is a quaternary ammonium salt or a quaternary phosphonium salt.

[3] The production method according to [1] or [2], wherein the onium salt is a quaternary ammonium salt.

[4] The production method according to any one of [1] to [3], wherein
$R^1$ is a linear or branched aliphatic hydrocarbon group having 1 to 3 carbons.

[5] The production method according to any one of [1] to [4], wherein
$R^1$ is a methyl group or an ethyl group.

[6] The production method according to any one of [1] to [5], wherein
the pH value in the reaction system in the step of oxidizing the carbon-carbon double bond is 3.0 to 7.0.

[7] The production method according to any one of [1] to [6],
further comprising a neutral inorganic salt in the reaction system of the step of oxidizing the carbon-carbon double bond.

[8] The production method according to any one of [1] to [7], wherein
the ratio of the selectivity of the by-product to the selectivity of the epoxy compound is 0.25 or less.

Effect of the Invention

According to the present invention, it is advantageous in that an epoxy compound can be produced efficiently. Further, according to the present invention, it is advantageous in that the epoxy compound can be produced safely and easily.

EMBODIMENT OF THE INVENTION

The method for producing an epoxy compound in the present invention comprises a step of oxidizing a carbon-carbon double bond in an organic compound with hydrogen peroxide in the presence of a catalyst, wherein the catalyst comprises a tungsten compound; a phosphoric acid, a phosphonic acid or salts thereof; and an onium salt having an alkyl sulfate ion represented by formula (I) as an anion:

wherein $R^1$ is a linear or branched aliphatic hydrocarbon group having 1 to 18 carbons, which may be substituted with 1 to 3 phenyl groups. That is, the method for producing an epoxy compound according to the present invention is characterized in that an onium salt having an alkyl sulfate ion represented by formula (I) as an anion is used as a phase transfer catalyst in a method for producing an epoxy compound by hydrogen peroxide using an organic compound having a carbon-carbon double bond as a raw material. This feature makes it possible to efficiently produce the epoxy compound while suppressing the formation of a by-product.

In the present specification, the method for producing an epoxy compound of the present invention is defined as a method for producing a product obtained by epoxidizing at least one double bond in an organic compound having a carbon-carbon double bond. Therefore, when the number of double bonds in the organic compound having a carbon-carbon double bond is defined as n, $2^n-1$ kinds of products can be obtained in the method for producing an epoxy compound of the present invention.

In the present specification, the by-product in the method for producing an epoxy compound of the present invention is a compound having a structure in which an epoxy ring is opened during the epoxidation reaction of the double bond. As an embodiment of a compound having such ring-opening structure, most of the compounds have a diol structure; however, there may also be included compounds having other structures generated by an epoxidation reaction in place of one or both hydroxyl groups of the diol structure, Therefore, according to the method for producing an epoxy compound of the present invention, even if a compound is obtained by epoxidizing at least one double bond in an organic compound having a carbon-carbon double bond, a compound having a structure in which an epoxy ring is opened in the same molecule does not fall under the category of an epoxy compound but under the category of a by-product.

In the method for producing an epoxy compound of the present invention, preferably, an epoxidation reaction of an organic compound having a substrate of a carbon-carbon double bond with hydrogen peroxide is carried out in a reaction system of a two-phase liquid consisted of an organic phase and an aqueous phase. In the method for producing an epoxy compound according to the present invention, a tungsten compound; a phosphoric acid, a phosphonic acid or salts thereof; and an onium salt having an alkyl sulfate ion represented by formula (I) as an anion act as a catalyst for the epoxidation reaction. In the reaction system of the two-phase liquid, catalysts other than the onium salt used in the present invention (i.e., a tungsten compound and a phosphoric acid, a phosphonic acid, or salts thereof), hydrogen peroxide, and a neutral inorganic salt to be added as necessary are water-soluble and therefore migrate to the aqueous phase, while the substrate and the onium salt are hardly soluble in water and form an organic phase. Therefore, an onium salt having an alkyl sulfate ion represented by formula (I) as an anion functions as a phase transfer catalyst. If necessary, an organic solvent may be added to the reaction system in order to improve the solubility and dispersibility of the substrate, to adjust the reaction rate, and to suppress the formation of the reaction by-product.

(1) Organic Compound Having Carbon-Carbon Double Bond

The organic compound having a carbon-carbon double bond used as a raw material in the method for producing an epoxy compound of the present invention is not particularly limited, as long as the organic compound has at least one carbon-carbon double bond in the molecule. For example, various organic compounds such as chain aliphatic organic compounds, alicyclic aliphatic organic compounds, or aromatic compounds can be used. These various organic compounds such as chain aliphatic organic compounds, alicyclic aliphatic organic compounds, and aromatic compounds can be used as a raw material, even if they have at least one epoxy group already in the molecule, as long as they further have at least one carbon-carbon double bond.

(1-1) Chain Aliphatic Organic Compound

The chain aliphatic compound having a carbon-carbon double bond used as a raw material in the method for producing an epoxy compound of the present invention may be a linear compound or a branched compound.

Examples of the chain aliphatic organic compound include alkenes having 2 to 40 carbons (preferably alkenes having 2 to 30 carbons and further preferably alkenes having 2 to 20 carbons) such as ethylene, propene, 1-butene, 2-butene, 1-pentene, 2-pentene, 1-hexene, 2-hexene, 2,3-dimethyl-2-butene, 3-hexene, 1-heptene, 2-heptene, 1-octene, 2-octene, 3-octene, 2-methyl-2-butene, 1-nonene, 2-nonene, decene, undecene, dodecene, tetradecene, hexadecene, and octadecene; alkadienes having 4 to 40 carbons (preferably alkadienes having 4 to 30 carbons and further preferably alkadienes having 4 to 20 carbons) such as butadiene, isoprene, 1,5-hexadiene, 1,6-heptadiene, 1,7-octadiene, 2,6-octadiene, decadiene, undecadiene and dodecadiene; and alkatrienes having 6 to 30 carbons (preferably alkatrienes having 6 to 20 carbons) such as undecatriene and dodecatriene. One of the linear or branched chain aliphatic organic compounds having a double bond may be used alone or two or more are possible in combination.

Examples of the chain aliphatic organic compound having a substituent include chain aliphatic organic compounds having an aryl group (for example, a phenyl group) as a substituent (for example, phenylethylene (or styrene), 1-phenylpropene, 2-phenyl-1-butene, 1-phenyl-1,3-butadiene, 1-phenyl-1,3-pentadiene, and the like). The chain aliphatic organic compound having an aryl group (for example, a phenyl group) as a substituent can also be referred to as an aromatic compound substituted with an alkenyl group (for example, an alkenyl group having 2 to 10 carbons (preferably an alkenyl group having 2 to 6 carbons) such as vinyl, allyl, propenyl, isopropenyl, and butenyl). As long as such aromatic compound has at least one double bond in the chain aliphatic organic compound which is a substituent, the aromatic compound may further be substituted with a substituent (for example, the substituents in the exemplification) in the alkenyl group portion and/or the aromatic ring portion, and may have a linking group between the alkenyl group portion and the aromatic ring portion. The linking group may be selected from the group consisting of carbonyl, ester, ether, amine, amide, silyl, sulfide, substituted or unsubstituted alkylene having 1 to 20 carbons and substituted or unsubstituted arylene having 6 to 40 carbons.

(1-2) Alicyclic Aliphatic Compound

There is no particular limitation to the alicyclic aliphatic organic compound having a carbon-carbon double bond used as a raw material in the method for producing an epoxy compound of the present invention, and use is possible to known alicyclic aliphatic organic compounds.

As an alicyclic aliphatic organic compound having a carbon-carbon double bond used as a raw material in the method for producing an epoxy compound of the present invention, suitable use can be made to a compound having two carbon-carbon double bonds represented by the following formulae (II) to (V).

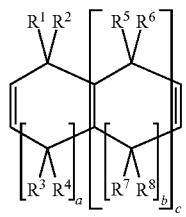

(II)

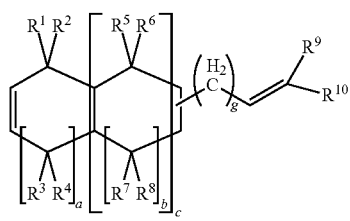

(III)

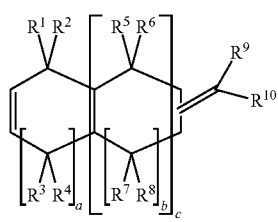

(IV)

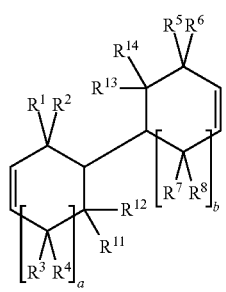

(V)

In formulae (II) to (V), a and b are each independently an integer from 0 to 5, more preferably an integer from 0 to 3, and further preferably 0 or 1.

In formulae (II) to (IV), c is an integer from 0 to 10, more preferably an integer from 0 to 5, and further preferably an integer of 1 to 3.

In the above formulae (II) to (IV), when c is 2 or more, b is selected independently.

In the above formulae (II) to (V), $R^1$, $R^2$, $R^3$ and $R^4$ each independently represent hydrogen or a straight or branched alkyl group having 1 to 30 carbons and preferably 1 to 10 carbons, and $R^1$ or $R^2$ and $R^3$ or $R^4$ may form a crosslinked structure represented by —$(CH_2)e$-. In the formula, e is an integer from 1 to 5 and more preferably an integer from 1 to 3. When a is 2 or more in formulae (II) to (V), $R^3$ and $R^4$ are selected independently. When a is 2 or more in formula (II) to formula (V), $R^3$ and $R^4$ will be present in an amount of 2 or more; however, the one which can form a crosslinked structure with either one of $R^1$ and $R^2$ is only $R^3$ or $R^4$ at any one position, and the other $R^1$, $R^2$, $R^3$ and $R^4$ are hydrogen or a linear or branched alkyl group having 1 to 30 carbons and preferably 1 to 10 carbons.

In the above formulae (II) to (V), $R^5$, $R^6$, $R^7$ and $R^8$ each independently represent hydrogen or a linear or branched alkyl group having 1 to 30 carbons an preferably 1 to 10 carbons, and $R^5$ or $R^6$ and $R^7$ or $R^8$ may form a crosslinked structure represented by —$(CH_{2f}$—. In the formula, f is an integer from 1 to 5 and more preferably an integer from 1 to 3.

In the above formulae (II) to (IV), when c is 2 or more, $R^5$, $R^6$, $R^7$ and $R^8$ are selected Independently. When b is 2. or more, $R^7$ and $R^8$ are selected independently.

When c is 1 or more and b is 2 or more in formulae (II) to (IV), $R^7$ and $R^8$ will be present in an amount of 2 or more; however, the one which can form a crosslinked structure with either one of $R^5$ and $R^6$ is only $R^7$ or $R^8$ at any position, and the other $R^5$, $R^6$, $R^7$ and $R^8$ are hydrogen or a linear or branched alkyl group having 1 to 30 carbons and preferably 1 to 10 carbons.

In formulae (III) and (IV), $R^9$ and $R^{10}$ each independently represent hydrogen or a straight or branched alkyl group having 1 to 30 carbons and preferably 1 to 10 carbons.

In the above formula (III), g is an integer from 0 to 8 and preferably an integer from 0 to 3. When g is 0, there is no methylene group and a single bond is formed.

In the above formula (V), $R^{11}$, $R^{12}$, $R^{13}$ and $R^{14}$ each independently represent hydrogen or a linear or branched alkyl group having 1 to 30 carbons and preferably 1 to 10 carbons.

Examples of the alicyclic aliphatic organic compound having a carbon-carbon double bond satisfying formula (II) include cyclopentadiene, cyclohexadiene, norbornadiene, dicyclopentadiene, tetrahydroindene, a compound represented by:

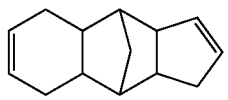 [SMILES: C1=CC2C3CC(C2C1)C1CC=CCC31]

a compound represented by:

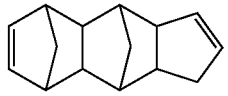 [SMILES: C1=CC2C(C1)C1CC2C2C3C=CC(C3)C12]

and a compound represented by:

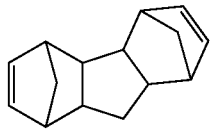 [SMILES: C1=CC2CC1C1CC3C4C=CC(C4)C3C21]

From the viewpoint of stability of the epoxy compound, preferred among these are those having two or more alicyclic rings, and preferred are norbornadiene, dicyclopentadiene, tetrahydroindene, a compound represented by the following formula:

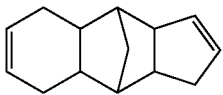 [SMILES: C1=CC2C3CC(C2C1)C1CC=CCC31]

a compound represented by the following formula:

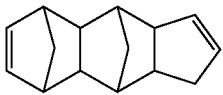

and a compound represented by the following formula:

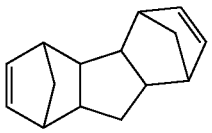 [SMILES: C1=CC2CC1C1CC3C4C=CC(C4)C3C21]

Examples of the alicyclic aliphatic organic compound having a carbon-carbon double bond satisfying formula (III) include vinyl cyclopentene, vinyl cyclohexene, vinyl norbornene, a compound represented by:

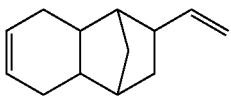

and a compound represented by the following formula:

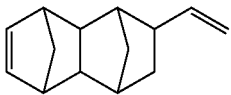

Examples of the alicyclic aliphatic organic compound having a carbon-carbon double bond satisfying formula (IV) include 5-ethylidene-2-norbornene and methylenecyclohexene, a compound represented by the following formula:

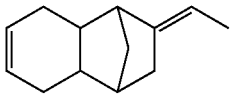

and a compound represented by the following formula:

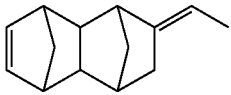

Examples of the alicyclic aliphatic organic compound having a carbon-carbon double bond satisfying formula (V) include a compound represented by the following formula:

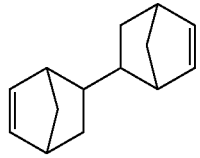 [SMILES: C1=CC2CC1CC2C1CC2C=CC1C2]

a compound represented by the following formula:

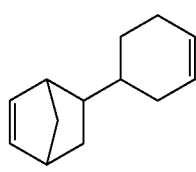 [SMILES: C1=CCC(C2CC3C=CC2C3)CC1]

and a compound represented by the following formula:

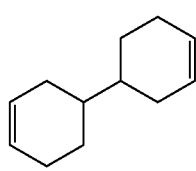 [SMILES: C1=CCC(C2CC=CCC2)CC1]

As for the alicyclic aliphatic organic compound having a carbon-carbon double bond used as a raw material in the method for producing an epoxy compound of the present invention, it is possible to use, for example, cyclopentene, cyclohexene, cycloheptene, cyclooctene, cyclodecene, cyclododecatriene, methylmethylenecydopropane, methylenecyclopentane, tetracyclododecene, norbornene, vinylcyclohexane, cyclooctadiene, methylenecyclopropane, methyldicyclopentadiene, and the like, apart from the compounds having two carbon-carbon double bonds represented by the above described formulae (II) to (V).

(1-3) Aromatic Compound

The aromatic compound having a carbon-carbon double bond used as a raw material in the method for producing an epoxy compound of the present invention is not particularly limited, as long as it is an aromatic compound having an ethylenic unsaturated double bond, and known aromatic compounds can be used. Examples of the aromatic compound having an ethylenic unsaturated double bond include indene-based aromatic compounds.

(2) Hydrogen Peroxide

The hydrogen peroxide used in the method for producing an epoxy compound of the present invention is not particularly limited, and known hydrogen peroxides can be used. Hydrogen peroxide is preferably used as an aqueous solution, that is, hydrogen peroxide water, from the viewpoint of handling and the like. The concentration of the aqueous solution of hydrogen peroxide used in the reaction is not limited, and is usually about 1 to 70 % by weight and preferably about 10 to 60 % by weight.

In the method for producing an epoxy compound of the present invention, the amount of hydrogen peroxide used Is not limited, but is usually about 0.5 to 4 equivalents and about preferably about 1 to 2.5 equivalents, with respect to the carbon-carbon double bond contained in the organic compound having the carbon-carbon double bond as a substrate.

(3) Tungsten Compound

The tungsten compound used in the method for producing an epoxy compound of the present invention is not particularly limited, as long as it is a tungsten compound capable of forming a tungstate anion in water and catalyzing the epoxidation reaction of a carbon-carbon double bond with hydrogen peroxide. Examples include tungstic acid, tungsten trioxide, tungsten trisulfide, tungsten hexachloride, phosphotungstic acid, silicotungstic acid and the like; and tungstates such as ammonium tungstate, potassium tungstate, sodium tungstate, calcium tungstate and the like. Preferred among these are tungstic acid, tungsten trioxide, phosphotungstic acid and sodium tungstate, and sodium tungstate dihydrate is particularly preferred. One of these tungsten compounds may be used alone or two or more are possible in combination.

The amount of the tungsten compound used in the method for producing the epoxy compound of the present invention is selected from the range of about 0.0001 to 20 mol % and preferably about 0.01 to 10 mol %, based on the organic compound having a carbon-carbon double bond in the molecule.

(4) Phosphoric Acid, Phosphonic Acid or Salts Thereof

Phosphoric acid, phosohonic acid or salts thereof The phosphoric acid, phosphonic acid or salts thereof used in the method for producing the epoxy compound of the present invention is not particularly limited, as long as the phosphoric acid, phosphonic acid or salts thereof can catalyze the epoxidation reaction of the carbon-carbon double bond with hydrogen peroxide. Examples of the phosphoric acid used in the method for producing an epoxy compound of the present invention include phosphoric acid, polyphosphoric acid, pyrophosphoric acid, hexametaphosphoric acid, hypophosphorous acid, phosphorous acid, dodecyl phosphoric acid, 2-ethylhexyl phosphoric acid, and the like. Examples of the salts of phosphates used in the method for producing the epoxy compound of the present invention include sodium phosphate, potassium phosphate, ammonium phosphate, sodium dihydrogen phosphate, disodium hydrogen phosphate, potassium hydrogen phosphate, ammonium hydrogen phosphate, sodium polyphosphate, sodium hexametaphosphate, acidic sodium hexametaphosphate, sodium polyphosphate, sodium pyrophosphate, disodium dihydrogen pyrophosphate, sodium hypophosphite, sodium phosphite, and the like. Examples of the phosphonic acid used in the method for producing the epoxy compound of the present invention include methylphosphonic acid, ethylphosphonic acid, n-propylphosphonic acid, isopropylphosphonic acid, n-butylphosphonic acid, t-butylphosphonic acid, phenylphosphonic acid, 4-methoxyphenylphosphonic acid, 4-aminophenytphosphonic acid, 1-hydroxyethane-1,1-bis (phosphonic acid), nitrilotris(methylenephosphonic acid), and the like. Examples of the salts of phosphonates used in the method for producing an epoxy compound of the present invention include sodium phenylphosphonate and the like.

From the viewpoint of availability and reaction activity, preferred among these are phosphoric acid, phenylphosphonic acid, phosphorous acid, hypophosphorous acid, 2-ethylhexyl phosphoric acid, lauryl phosphoric acid, sodium dihydrogen phosphate, and the like, and particularly preferred is phenylphosphonic acid. In the present invention, one selected from the group consisting of the above-mentioned phosphoric acids, phosphonic acids or salts thereof can be used alone or two or more are possible in combination.

The amount of the phosphoric acid, phosphonic acid or salts thereof used in the method for producing the epoxy compound of the present invention is selected from the range of about 0.0001 to 10 mol % and preferably about 0.01 to 10 mol %, with respect to the organic compound having a carbon-carbon double bond in the molecule.

(5) Onium Salt Having an Alkyl Sulfate Ion Represented by Formula (I) as an Anion As the onium salt having an alkyl sulfate ion represented by formula (I) as an anion used in the method for producing an epoxy compound of the present invention, any onium salts can be used as long as they function as a phase transfer catalyst in the epoxidation reaction of a carbon-carbon double bond with hydrogen peroxide. Examples of such onium salts include quaternary ammonium salts, quaternary ammonium salts containing nitrogen rings, quaternary phosphonium salts, quaternary sulfonium salts, macrocyclic polyethers, and the like. Preferred among these are quaternary ammonium salts and quaternary phosphonium salts.

(5-1) Cation of Onium Salt

Examples of the cations of the quaternary ammonium salts include those having aryl groups and those consisted of alkyl groups. Examples of those having aryl groups include benzyltrimethylammonium, benzyltriethylammonium, benzyltributylammonium, phenyltrimethylammonium, lauryldimethylbenzylammonium, and the like. Examples of those consisted of alkyl groups include tetramethylammonium, tetraethylammonium, tetrapropylammonium, tetrabutylammonium, tetrahexylammonium, tetraoctylammonium, trioctylmethylammonium, trioctylethyiammonium, dilauryldimethyiammonium, didecyldimethylammonium, didecyldiethylammonium, didecyldipropylammonium, dioleyldimethylammonium, lauryltrimethylammonium, distearyl dimethylammonium, stearyl trimethylammonium, dioctadecyldimethylammonium, octadecyltrimethyiammonium, dicetyldimethylammonium, cetyltrimethylammonium, tricaprylmethylammonium, palmityldimethylethylammonium, hexadecyltrimethylammonium, lauryldimethylammonium, and the like. From the viewpoint of solubility In an organic solvent, preferred among these are those consisted of alkyl groups, and more preferred are those in which the total number of carbon atoms contained in the alkyl group is 16 or more.

Further, from the viewpoint of catalytic activity, preferred are those having a long-chain alkyl group having 8 or more carbon atoms, and more preferred are those in which the difference between the number of carbon atoms in the long-chain alkyl group having the largest number of carbon atoms and the number of carbon atoms in the alkyl group having the smallest number of carbon atoms is 7 or more, specific examples being, preferably, trioctylmethylammonium, dilauryldimethylammonium, didecyldimethylammonium, didecyldiethylammonium, didecyldipropylammonium, dioleyldimethylammonium, lauryltrimethylammonium, distearyl dimethylammonium, stearyl trimethylammonium, dioctadecyldimethylammonium, octadecyldimethylammonium, dicetyldimethylammonium, cetyltrimethylammonium, tricaprylmethylammonium, palmityldimethylethylammonium, and lauryldimethylethylammonium.

Examples of the cations of the quaternary ammonium salts containing nitrogen rings include quaternary ammonium salts in which the nitrogen rings are consisted of nitrogen-containing heterocyclic rings such as pyridine rings, picoline rings, quinoline rings, imidazoline rings, or morpholine rings. Preferred among these are quaternary ammoniums comprising pyridine rings. Specific examples include alkyl (straight or branched alkyl having 8 to 20 carbons, as like in the description of the cations of the following quaternary ammonium salts containing nitrogen rings), pyridinium (for example, N-lauryl pyridinium, N-cetyl pyridinium, and the like), alkylpicorium (for example, N-lauryl picorinium), alkyl quinolinium, alkylisoquinolinium, alkylhydroxyethyl imidazoline, alkylhydroxymorpholine, and the like.

Examples of the cations of the quaternary phosphonium salts include tetramethylphosphonium, tetrabutylphosphonium, tributyl (hexadecyl) phosphonium, triethylphenylphosphonium, and the like.

Examples of the cations of the quaternary sulfonium salts include triethylsulfoniumiodide, ethyldiphenylsulfoniumiodide, and the like.

(5-2) Anion of Onium Salt

The anion of an onium salt used in the method for producing an epoxy compound of the present invention is an alkyl sulfate ion represented by formula (I):

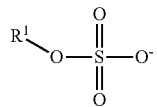

(I)

wherein $R^1$ is a linear or branched aliphatic hydrocarbon group having 1 to 18 carbons, optionally substituted by 1 to 3 phenyl groups.

In formula (I), $R^1$ represents a linear or branched aliphatic hydrocarbon group having 1 to 18 carbons, preferably a linear or branched aliphatic hydrocarbon group having 1 to 12 carbons, more preferably 1 to 6 carbons, more particularly 1 to 3 carbons, and more particularly preferably a methyl group or an ethyl group. Further, such a linear or branched aliphatic hydrocarbon group may be substituted by 1 to 3 phenyl groups, preferably 1 to 2 phenyl groups, and more preferably 1 phenyl group.

Accordingly, examples of $R^1$ in formula (I) include benzyl groups, isopropyl groups, normal propyl groups, ethyl groups, methyl groups, and the like.

From the viewpoint of availability, preferred among these for the anion of the onium salt used in the method for producing an epoxy compound of the present invention are alkyl sulfate ions having 1 to 3 carbons, such as methyl sulfate ions, ethyl sulfate ions, and propyl sulfate ions, and particularly preferably methyl sulfate ions or ethyl sulfate ions.

(5-3) Onium Salt

As for the onium salt used in the method for producing an epoxy compound of the present invention, it is possible to appropriately combine and use from the above-described onium salt cations and onium salt anions. With respect to the onium salt selected as described above, it is possible to use one from the above singularly or two or more in combination.

The onium salt used in the method for producing an epoxy compound of the present invention can be synthesized by a known method. For example, as disclosed in JPH9-67320, it can be synthesized by reacting a tertiary amine with dialkyl sulfuric acid using a nonionic surfactant as a reaction solvent.

The amount of onium salt used in the method for producing the epoxy compound of the present invention is selected from the range of about 0.0001 to 20 mol % and preferably about 0.01 to 10 mol % with respect to the organic compound having a carbon-carbon double bond in the molecule.

(6) Organic Solvent

In the method for producing an epoxy compound of the present invention, an organic solvent may be added to the reaction system as necessary in order to improve the solubility and dispersibility of the substrate, to adjust the reaction rate, and to suppress the formation of reaction by-products. In particular, when the olefin compound is a solid, it is preferable to use a reaction solution containing an organic solvent from the viewpoint of improving operability.

When an organic solvent is used In the method for producing an epoxy compound of the present invention, the organic compound having a carbon-carbon double bond in the molecule may be dissolved or be in a suspended state in the organic solvent; however, it is usually preferable that the organic compound is dissolved in the organic solvent under reaction temperature conditions.

The organic solvent used in the present invention is not particularly limited as long as it is inert to the organic compound to be used or the active catalyst, and specific examples thereof include aromatic hydrocarbons such as benzene, toluene and xylene; aliphatic hydrocarbons such as hexane (including cyclohexane and n-hexane), heptane, octane and dodecane; alcohols such as methanol, ethanol, isopropanol, butanol, hexanol and cyclohexanol; halogen solvents such as chloroform, dichloromethane and dichloroethane; ethers such as tetrahydrofuran and dioxane; ketones such as methyl ethyl ketone, methyl isobutyl ketone, cyclopentanone and cyclohexanone; nitriles such as acetonitrile and butyronitrile; esters such as ethyl acetate, butyl acetate and methyl formate; amides such as N,N-dimethylformamide and N,N-dimethylacetamide; ureas such as N,N'-dimethyl imidazolidinone; and mixtures of these solvents, and preferred are aromatic hydrocarbons, aliphatic hydrocarbons or mixtures thereof. Further, preferred are aromatic hydrocarbons which are stable to the reaction, and more preferred is toluene having a boiling point higher than the reaction temperature. This is because, when an active catalyst having a particularly high reaction activity is used, it is preferable in terms of the efficiency of reaction and operation to carry out a two-phase reaction using an organic solvent forming a two-phase system with water.

With respect to the amount of the organic solvent used in the present invention, the organic solvent can be used, without particular limitation, upon appropriate adjustment depending on the solubility and various physical properties of the organic compound, and from the viewpoint of productivity and safety, the use amount is about 1 to 500 mol %, preferably about 10 to 300 mol %, or 5 times or less, and preferably 3 times or less, of the organic compound having a carbon-carbon double bond in the molecule.

(7) Neutral Inorganic Salt

Epoxidation reaction of a carbon-carbon double bond may be carried out in the method for producing an epoxy compound of the present invention as necessary, in the presence of a neutral inorganic salt. Examples of such neutral inorganic salt include sulfates, nitrates, carbonates, and phosphates. From the viewpoint of availability, preferred is sulfate, more preferred are lithium sulfate, sodium sulfate, potassium sulfate, calcium sulfate, magnesium sulfate and the like, and particularly preferred are sodium sulfate, lithium sulfate and the like.

The neutral inorganic salt may be an anhydride, a hydrate, or a mixture thereof.

One of the neutral inorganic salts may be used alone or two or more are possible in combination. The amount of the neutral inorganic salt used is selected from the range of about 0.1 to 500 mol % and preferably about 1 to 50 mol % with respect to the organic compound having a carbon-carbon double bond in the molecule.

(8) Epoxidation Reaction

(8-1) pH in Reaction System

In the method for producing an epoxy compound of the present invention, the pH value of the aqueous phase in the reaction system is preferably 3.0 to 7.0, more preferably 4.0 to 7.0, and particularly preferably 4.5 to 7.0 or 4.0 to 6.5, from the viewpoint of improving the rate of the epoxidation reaction and suppressing the formation of by-products. According to the catalyst composition, when the pH in the reaction system is not within the above range, the pH in the reaction system can be adjusted within the above range using an acid such as sulfuric acid, an acidic salt such as phosphate, an alkali metal hydroxide such as sodium hydroxide, or the like, to carry out the epoxidation reaction.

(8-2) Region Temperature and Reaction Time

In the method for producing an epoxy compound of the present invention, the reaction temperature is usually about 0 to 80° C., preferably about 20 to 50° C., and more preferably about 30 to 40° C.

The reaction time in the method for producing an epoxy compound of the present invention may be appropriately determined depending on the amount of the catalyst used, the reaction temperature and the like, and is usually about 1 to 50 hours and preferably about 5 to 30 hours.

(8-3) Procedure of Epoxidation Reaction

In carrying out the method for producing an epoxy compound of the present invention, it is possible to carry out the epoxidation reaction by, for example, introducing into the reaction system an organic compound having a carbon-carbon double bond; a tungsten compound; a phosphoric acid, a phosphonic acid or salts thereof; an onium salt having an alkyl sulfate ion represented by formula (I) as an anion; and optionally an organic solvent and/or a neutral inorganic salt for mixture, adding hydrogen peroxide dropwise thereto, and stirring the mixture at a predetermined temperature. This order of addition may be changed, if necessary.

(8-4) Treatment After Epoxidation Reaction

After completion of the reaction, the product is separated by a known method and optionally purified, so that the epoxy compound of interest is obtained. For example, the target epoxy compound can be obtained from the product by distillation. Alternatively, when the product is a solid, the desired product can be obtained by crystallization from a solvent containing the product. If necessary, residual hydrogen peroxide may be decomposed with an aqueous solution of sodium thiosulfate or the like.

(8-5) Index of Efficiency of Epoxidation Reaction

Thus, an epoxy compound can be obtained in high conversion, selectivity and yield from a compound having a carbon-carbon double bond, according to the method for producing an epoxy compound of the present invention. The epoxy compound can be quantitatively analyzed by an internal standard method using an internal standard substance of nonane by gas chromatography.

As used herein, "yield of an epoxy compound" can be calculated by the following.

Yield of epoxy compound=(number of moles of epoxy compound obtained after reaction)/(number of moles of olefin charged)×100

"Yield of a by-product" can be calculated by the following.

Yield of by-product=((number of moles of olefin charged)−(number of moles of epoxy compound obtained after reaction))/(number of moles of olefin charged)×100

Therefore, "selectivity of an epoxy compound" can be calculated by the following.

Selectivity of epoxy compound=(yield of epoxy compound)/(conversion ratio of charged olefin)×100

"Selectivity of by-product" can be calculated by the following.

Selectivity of by-product=(yield of by-product)/(conversion ratio of charged olefin)×100

According to a preferred embodiment of the method for producing an epoxy compound of the present invention, the selectivity of the by-product to the selectivity of the epoxy compound is 0.25 or less, and in a further preferred embodiment, is 0.1 or less.

EXAMPLES

Hereinafter, the present invention shall be described in more details with reference to the Examples; however, the present invention shall not be limited to these Examples.

Example 1

To a reaction vessel equipped with a thermometer, a stirrer, a reflux pipe, and a dropping device were introduced, 25.9 g of a diolefin compound represented by formula (1), 6.58 g of toluene, 1.42 g of sodium tungstate dihydrate, 2.12 g of trioctylmethylammonium methylsulfate, 0.694 g of phenylphosphonic acid, and 2.81 g of anhydrous sodium sulfate, and then 32.7 g of 45% hydrogen peroxide water was dropped over 4 hours while stirring at 25° C., and the reaction was carried out at 30° C. for 7 hours. The pH of the reaction solution during the reaction was 4.0 to 6.5. After the reaction, gas chromatography analysis showed that conversion of the compound represented by formula (1) was 96%, selectivity of the epoxy compounds represented by formulae (2) to (4) was 91% (yield: 86%), and selectivity of the by-product was 9% (yield: 8%).

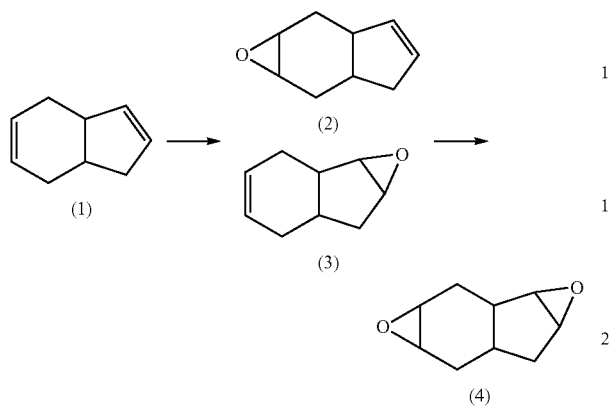

Example 2

To a reaction vessel equipped with a thermometer, a stirrer, a reflux pipe, and a dropping device were introduced, 25.9 g of a diolefin compound represented by formula (1), 6.6 g of toluene, 1.43 g of sodium tungstate dihydrate, 1.88 g of didecyldimethylammonium methyl sulfate, 0.69 g of phenylphosphonic acid, and 2.76 g of anhydrous sodium sulfate, and then 32.7 g of 45% hydrogen peroxide water was dropped over 4 hours while stirring at 25° C., and the reaction was carried out at 30° C. for 7 hours. The pH of the reaction solution during the reaction was 4.7 to 6.5. After the reaction, gas chromatography analysis showed that conversion of the compound represented by formula (1) was 97%, selectivity of the epoxy compounds represented by formulae (2) to (4) was 92% (yield: 90%), and selectivity of the by-product was 8% (yield: 8%).

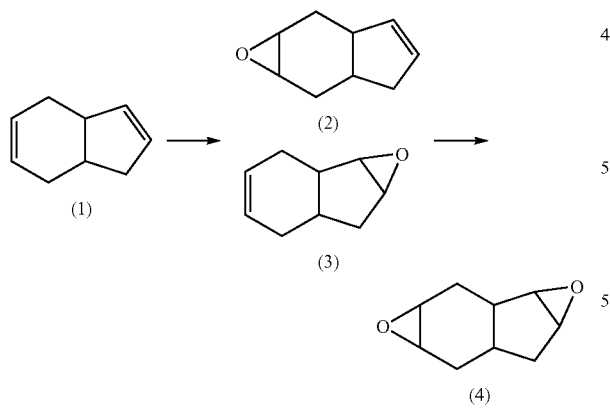

Example 3

To a reaction vessel equipped with a thermometer, a stirrer, a reflux pipe, and a dropping device were introduced, 25.8 g of a diolefin compound represented by formula (1), 6.6 g of toluene, 1.43 g of sodium tungstate dihydrate, 1.93 g of didecyldimethylammonium methylsulfate, and 0.72 g of phenylphosphonic acid, and then 32.8 g of 45% hydrogen peroxide water was dropped over 4 hours while stirring at 25° C., and the reaction was carried out at 30° C. for 7 hours. The pH of the reaction solution during the reaction was 4.1 to 5.3. After the reaction, gas chromatography analysis showed that conversion of the compound represented by formula (1) was 99%, selectivity of the epoxy compounds represented by formulae (2) to (4) was 84% (yield: 83%), and selectivity of the by-product was 16% (yield: 16%).

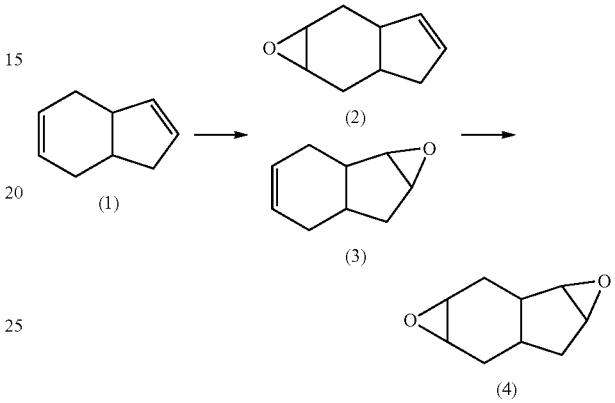

Example 4

To a reaction vessel equipped with a thermometer, a stirrer, a reflux pipe, and a dropping device were introduced, 25.9 g of a diolefin compound represented by formula (1), 6.59 g of toluene, 1.44 g of sodium tungstate dihydrate, 1.88 g of palmityldimethylethyl ammonium-ethyl sulfate, 0.679 g of phenylphosphonic acid, and 2.76 g of anhydrous sodium sulfate, and then 32.7 g of 45% hydrogen peroxide water was dropped over 4 hours while stirring at 25° C., and the reaction was carried out at 30° C. for 7 hours. The pH of the reaction solution during the reaction was 3.8 to 5.6. After the reaction, gas chromatography analysis showed that conversion of the compound represented by formula (1) was 86%, selectivity of the epoxy compounds represented by formulae (2) to (4) was 81% (yield: 69%), and selectivity of the by-product was 19% (yield: 16%).

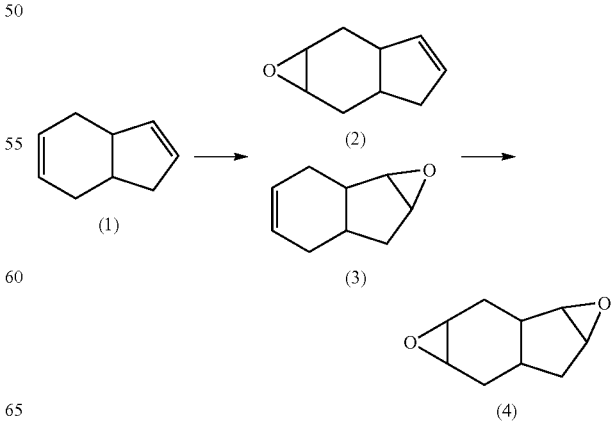

Example 5

To a reaction vessel equipped with a thermometer, a stirrer, a reflux pipe, and a dropping device were introduced, 2.00 g of a diolefin compound represented by formula (5), 0.510 g of toluene, 69.2 mg of sodium tungstate dihydrate, 99.0 mg of hexadecyltrimethylammonium methyl sulfate, 32.3 mg of phenylphosphonic acid, 139.3 mg of anhydrous sodium sulfate, and 1.60 g of 45% hydrogen peroxide water, and the reaction was carried out at 30° C. for 11 hours. The pH of the reaction solution during the reaction was 3.8 to 4.1. After the reaction, gas chromatography analysis showed that conversion of the compound represented by formula (5) was 83%, selectivity of the epoxy compound represented by formulae (6) to (8) was 99% (yield: 81%), and selectivity of the by-product was 1% (yield: 1%).

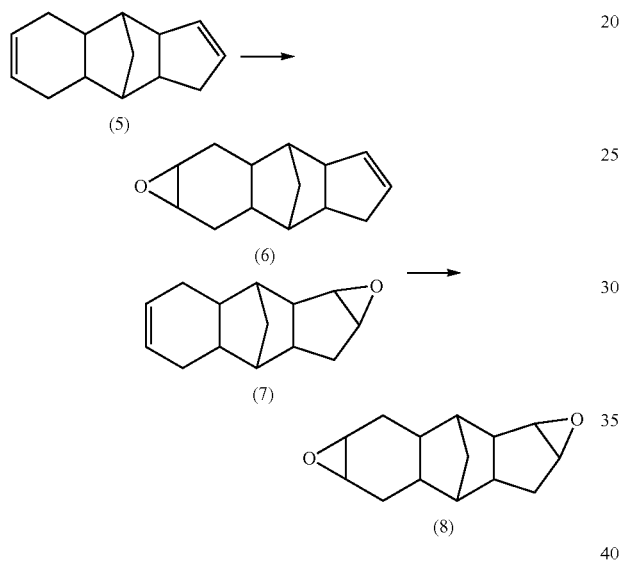

Example 6

To a reaction vessel equipped with a thermometer, a stirrer, a reflux pipe, and a dropping device were introduced, 2.01 g of a diolefin compound represented by formula (5), 0.505 g of toluene, 72.3 mg of sodium tungstate dihydrate, 116 mg of lauryl dimethylethylammonium ethyl sulfate, 33.9 g of phenylphosphonic acid, 136.8 of anhydrous sodium sulfate, and 1.60 g of 45% hydrogen peroxide water, and the reaction was carried out at 30° C. for 11 hours. The pH of the reaction solution during the reaction was 3.8 to 4.1. After the reaction, analysis by gas chromatography showed that conversion of the compound represented by formula (5) was 87%, selectivity of the epoxy compound represented by formulae (6) to (8) was 91% (yield: 79%), and selectivity of the by-product was 9% (yield: 8%).

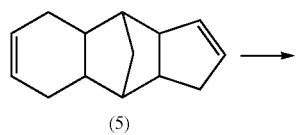

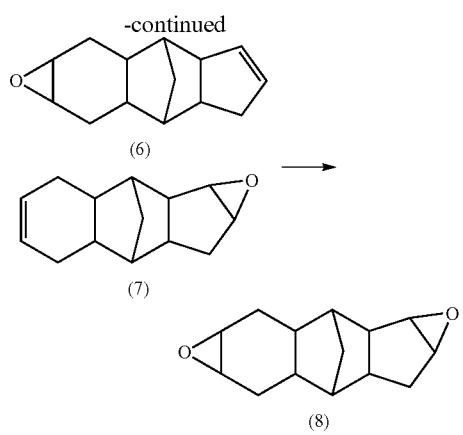

Example 7

To a reaction vessel equipped with a thermometer, a stirrer, a reflux pipe, and a dropping device were added, 2.01 g of a diolefin compound represented by formula (5), 0.502 g of toluene, 70.5 g of sodium tungstate dihydrate, 63.9 mg of palmityldimethylethyl ammonium-ethyl sulfate, 35.9 mg of phenylphosphonic acid, 139.8 mg of anhydrous sodium sulfate, and 1.60 g of 45% hydrogen peroxide water, and the reaction was carried out at 30° C. for 11 hours. The pH of the reaction solution during the reaction was 3.8 to 4.1. After the reaction, analysis by gas chromatography showed that the conversion of the compound represented by formula (5) was 87%, selectivity of the epoxy compound represented by formulae (6) to (8) was 88% (yield: 76%), and selectivity of the by-product was 13% (yield: 11%).

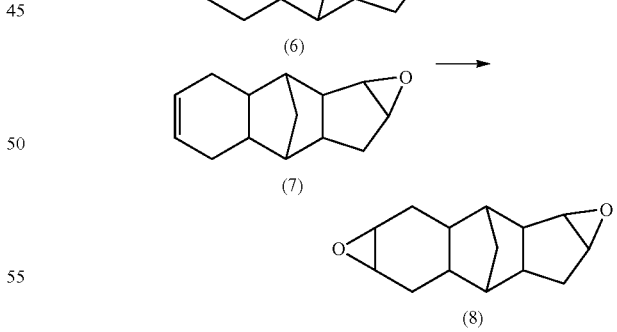

Example 8

To a reaction vessel equipped with a thermometer, a stirrer, a reflux pipe, and a dropping device were added, 2.05 g of a diolefin compound represented by formula (9), 0.604 g of toluene, 117 mg of sodium tungstate dihydrate, 240 mg of lauryl dimethylethylammonium ethyl sulfate, 60.0 mg of phenylphosphonic acid, 241 mg of anhydrous sodium sulfate, and 1.40 g of 45% hydrogen peroxide water, and then the reaction was carried out at 30° C. for 11 hours. The pH of the reaction solution during the reaction was 3.8 to 4.1. After the reaction, gas chromatography analysis showed that conversion of the compound represented by formula (9) was 79%, selectivity of the epoxy compound represented by formulae (10) to (12) was 93% (yield: 74%), and selectivity of the by-product was 7% (yield: 6%).

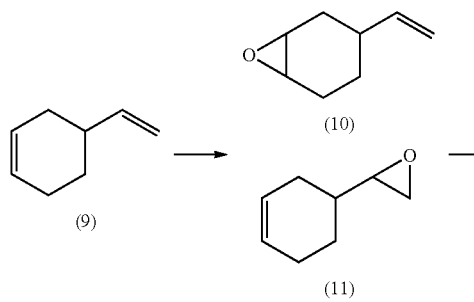

Example 9

To a reaction vessel equipped with a thermometer, a stirrer, a reflux pipe, and a dropping device were introduced, 1.99 g of a diolefin compound represented by formula (9), 0.513 g of toluene, 126 mg of sodium tungstate dihydrate, 192 mg of palmityldimethylethyl ammonium-ethyl sulfate, 60.0 mg of phenylphosphonic acid, 21 mg of anhydrous sodium sulfate, and 1.40 g of 45% aqueous hydrogen peroxide, and the reaction was carried out at 30° C. for 11 hours. The pH of the reaction solution during the reaction was 3.8 to 4.1. After the reaction, gas chromatography analysis showed that conversion of the compound represented by formula (9) was 79%, selectivity of the epoxy compound represented by formulae (10) to (12) was 97% (yield: 76%), and selectivity of the by-product was 3% (yield: 3%).

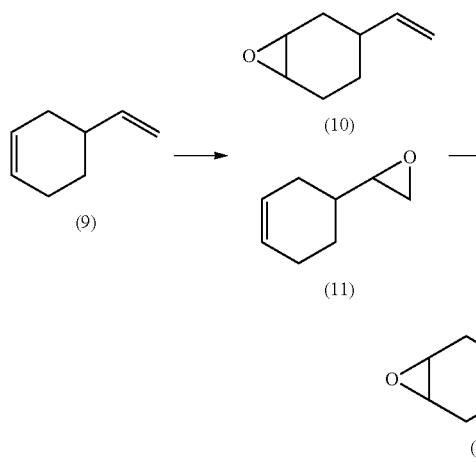

Example 10

To a reaction vessel equipped with a thermometer, a stirrer, a reflux pipe, and a dropping device were added, 2.02 g of a diolefin compound represented by formula (9), 0.503 g of toluene, 136 mg of sodium tungstate dihydrate, 159 mg of hexadecyltrimethylammonium methyl sulfate, 56.0 mg of phenylphosphonic acid, 230 mg of anhydrous sodium sulfate, and 1.40 g of 45% hydrogen peroxide water, and the reaction was carried out at 30° C. for 11 hours. The pH of the reaction solution during the reaction was 3.8 to 4.1. After the reaction, gas chromatography analysis showed that conversion of the compound represented by formula (9) was 72%, selectivity of the epoxy compound represented by formulae (10) to (12) was 98% (yield: 71%), and selectivity of the by-product was 2% (yield: 1%).

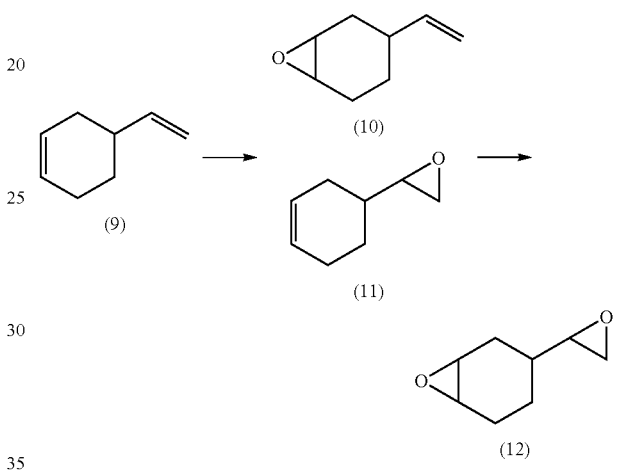

Comparative Example 1

To a reaction vessel equipped with a thermometer, a stirrer, a reflux pipe, and a dropping device were introduced, 25.9 g of a diolefin compound represented by formula (1), 6.5 g of toluene, 1.41 g of sodium tungstate dihydrate, 1.99 g of trioctylmethylammonium hydrogen sulfate, 0.344 g of phenylphosphonic acid, and 2.75 g of anhydrous sodium sulfate, and subsequently, 32.67 g of 45% hydrogen peroxide water was dropped over 4 hours while stirring at 25° C., and the reaction was carried out at 30° C. for 7 hours. The pH of the reaction solution during the reaction was 1.3 to 2.7. After the reaction, gas chromatography analysis showed that conversion of the compound represented by formula (1) was 96%, the selectivity of the epoxy compounds represented by formulae (2) to (4) was 74% (yield: 72%), and selectivity of the by-product was 26% (yield: 25%).

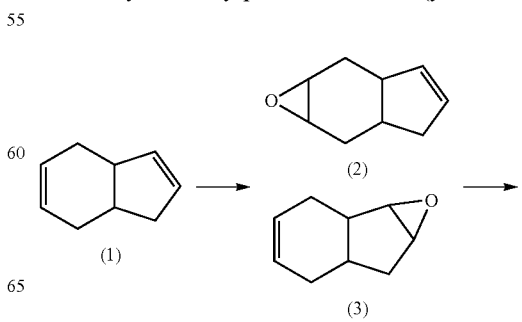

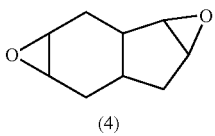

(4)

Comparative Example 2

To a reaction vessel equipped with a thermometer, a stirrer, a reflux pipe, and a dropping device were introduced, 25.8 g of a diolefin compound represented by formula (1), 6.6 g of toluene, 1.43 g of sodium tungstate dihydrate, 1.55 g of didecyldimethylammonium chloride, 0.72 g of phenylphosphonic acid, and 2.76 g of anhydrous sodium sulfate, and then 32.7 g of 45% hydrogen peroxide water was dropped over 4 hours while stirring at 25° C., and the reaction was carried out at 30° C. for 7 hours. The pH of the reaction solution during the reaction was 3.8 to 5.6. After the reaction, gas chromatography analysis showed that conversion of the compound represented by formula (1) was 74%, selectivity of the epoxy compounds represented by formulae (2) to (4) was 86% (yield: 64%), and selectivity of the by-product was 14% (yield: 10%).

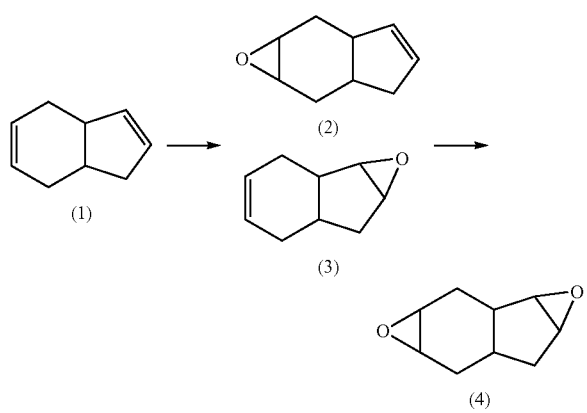

Comparative Example 3

To a reaction vessel equipped with a thermometer, a stirrer, a reflux pipe, and a dropping device were introduced, 25.8 g of a diolefin compound represented by formula (1), 6.46 g of toluene, 1.42 g of sodium tungstate dihydrate, 1.55 g of didecyldimethylammonium chloride, 0.648 g of phenylphosphonic acid, and 2.80 g of anhydrous sodium sulfate, and then 32.7 g of 45% hydrogen peroxide water was dropped over 4 hours while stirring at 25° C., and the reaction was carried out at 30° C. for 7 hours. The pH of the reaction solution during the reaction was 2.8 to 3.8. After the reaction, gas chromatography analysis showed that conversion of the compound represented by formula (1) was 95%, selectivity of the epoxy compounds represented by formulae (2) to (4) was 29% (yield: 28%), and selectivity of the by-product was 71% (yield: 67%).

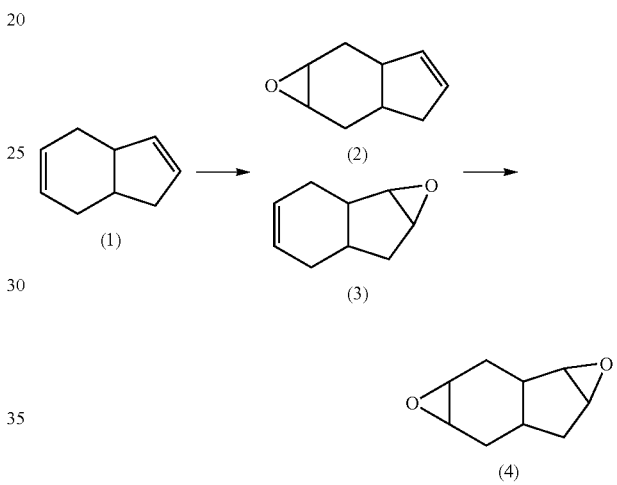

The results of Examples 1 to 10 and Comparative Examples 1 to 3 are as shown in Tables 1 and 2 below. An epoxy yield of 65% or more and a by-product yield of 20% or less were judged as acceptable.

TABLE 1

The results of Examples 1 to 4 and Comparative Examples 1 to 3

| | Example 1 | Example 2 | Example 3 | Example 4 | Comparative Example 1 | Comparative Example 2 | Comparative Example 3 |
|---|---|---|---|---|---|---|---|
| Chemical structure of organic compound having carbon-carbon double bond | Formula (1) | Formula (1) | Formula (1) | Formula (1) | Formula (1) | Formula (1) | Formula (1) |
| Alkyl group of quaternary ammonium of onium salt | Trioctyl-methyl | Didecyldi-methyl | Didecyldi-methyl | Palmityldi-methylethyl | Trioctyl-methyl | Didecyldi-methyl | Didecyldi-methyl |
| Anion of onium salt | Methyl sulfate | Methyl sulfate | Methyl sulfate | Ethyl sulfate | Hydrogen sulfate | chloride | chloride |
| Anhydrous sodium salt | Included | Included | Not included | Included | Included | Included | Included |
| pH | 4.0-6.5 | 4.7-6.5 | 4.1-5.3 | 3.8-5.6 | 1.3-2.7 | 3.8-5.6 | 2.8-3.8 |
| conversion ratio | 96 | 97 | 99 | 86 | 96 | 74 | 95 |
| selectivity of epoxy compound (%) | 91 | 92 | 84 | 81 | 74 | 86 | 29 |
| Yield of epoxy compound (%) | 86 | 90 | 83 | 69 | 72 | 64 | 28 |
| selectivity of by-product (%) | 9 | 8 | 16 | 19 | 26 | 14 | 71 |

TABLE 1-continued

The results of Examples 1 to 4 and Comparative Examples 1 to 3

|  | Example 1 | Example 2 | Example 3 | Example 4 | Comparative Example 1 | Comparative Example 2 | Comparative Example 3 |
|---|---|---|---|---|---|---|---|
| Yield of by-product (%) | 8 | 8 | 16 | 16 | 25 | 10 | 67 |
| selectivity of by-product/ selectivity of epoxy compound | 0.09 | 0.08 | 0.19 | 0.23 | 0.34 | 0.16 | 2.42 |

TABLE 2

The results of Examples 5 to 10

|  | Example 5 | Example 6 | Example 7 | Example 8 | Example 9 | Example 10 |
|---|---|---|---|---|---|---|
| Chemical structure of organic compound having carbon-carbon double bond | Formula (5) | Formula (5) | Formula (5) | Formula (5) | Formula (5) | Formula (5) |
| Alkyl group of quaternary ammonium of onium salt | Hexadecyl-trimethyl | Lauryldi-methylethyl | Palmityldi-methylethyl | Lauryldi-methylethyl | Palmityldi-methylethyl | Hexadecyl-trimethyl |
| Anion of onium salt | Methyl sulfate | Ethyl sulfate | Ethyl sulfate | Ethyl sulfate | Ethyl sulfate | Methyl sulfate |
| Anhydrous sodium salt | Included | Included | Included | Included | Included | Included |
| pH | 3.8-4.1 | 3.8-4.1 | 3.8-4.1 | 3.8-4.1 | 3.8-4.1 | 3.8-4.1 |
| conversion ratio | 83 | 87 | 87 | 79 | 79 | 72 |
| Selectivity of epoxy compound (%) | 99 | 91 | 87 | 93 | 97 | 98 |
| Yield of epoxy compound (%) | 81 | 79 | 76 | 74 | 76 | 71 |
| Selectivity of by-product (%) | 1 | 9 | 13 | 7 | 3 | 2 |
| Yield of by-product (%) | 1 | 8 | 11 | 6 | 3 | 1 |
| selectivity of by-product/ selectivity of epoxy compound | 0.01 | 0.10 | 0.14 | 0.08 | 0.03 | 0.02 |

According to the results shown in Tables 1 and 2 above, the following can be considered.

Comparing the results of Example 1 and Comparative Example 1, Example 1 using a methyl sulfate ion as an anion of an onium salt tended to have a lower yield of by-product than Comparative Example 1 which used hydrogen sulfate. This suggests that an efficient epoxidation reaction with less by-product is possible when a methyl sulfate ion is used as the anion of the onium salt.

Comparing the results of Example 2 with Comparative Examples 2 and 3, Example 2 using a methyl sulfate ion as an anion of an onium salt tended to have a higher epoxy selectivity than Comparative Examples 2 and 3 which used chloride. This suggests that an efficient epoxidation reaction with high epoxy selectivity is possible when a methyl sulfate ion is used as the anion of the onium salt.

According to the results of Examples 1 to 10, it has been suggested that as long as the methyl sulfuric acid or ethyl sulfuric acid is used as the anion of the onium salt, an efficient epoxidation reaction is possible with an epoxy yield of 65% or more and a by-product yield of 20% or less, regardless of the chemical structure of the organic compound having a carbon-carbon double bond and regardless of the number of carbons in the alkyl group of the cation (quaternary ammonium) of the onium salt or the number of long-chain alkyl groups having 8 or more carbons, and further regardless of whether or not anhydrous sodium sulfate is contained as the neutral inorganic salt.

The invention claimed is:

1. A method for producing an epoxy compound, comprising a step of oxidizing a carbon-carbon double bond in an organic compound with hydrogen peroxide in the presence of a catalyst and a neutral inorganic salt,
   wherein the catalyst comprises a tungsten compound; a phosphoric acid, a phosphonic acid or salts thereof; and an onium salt having an alkyl sulfate ion represented by formula (I) as an anion:

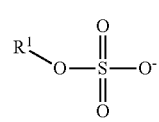
(I)

wherein $R^1$ is a linear or branched aliphatic hydrocarbon group having 1 to 18 carbons, which may be substituted with 1 to 3 phenyl groups, and wherein the ratio of the selectivity of the by-product to the selectivity of the epoxy compound is 0.25 or less.

2. The production method according to claim 1, wherein the onium salt is a quaternary ammonium salt or a quaternary phosphonium salt.

3. The production method according to claim 1, wherein the onium salt is a quaternary ammonium salt.

4. The production method according to claim 1, wherein $R^1$ is a linear or branched aliphatic hydrocarbon group having 1 to 3 carbons.

5. The production method according to claim 1, wherein $R^1$ is a methyl group or an ethyl group.

6. The production method according to claim 1, wherein the pH value in the reaction system in the step of oxidizing the carbon-carbon double bond is 3.0 to 7.0.

7. The production method according to claim 1, wherein the ratio of the selectivity of the by-product to the selectivity of the epoxy compound is 0.1 or less.

8. The production method according to claim 2, wherein the onium salt is a quaternary phosphonium salt.

9. The production method according to claim 2, wherein $R^1$ is a linear or branched aliphatic hydrocarbon group having 1 to 3 carbons.

10. The production method according to claim 2, wherein $R^1$ is a methyl group or an ethyl group.

11. The production method according to claim 3, wherein $R^1$ is a linear or branched aliphatic hydrocarbon group having 1 to 3 carbons.

12. The production method according to claim 11, wherein $R^1$ is a methyl group or an ethyl group.

13. The production method according to claim 12, wherein the pH value in the reaction system in the step of oxidizing the carbon-carbon double bond is 3.0 to 7.0.

14. The production method according to claim 1, wherein the neutral inorganic salt comprises a sulfate, a nitrate, a carbonate, or a phosphate.

15. The production method according to claim 1, wherein the neutral inorganic salt comprises a sulfate.

16. The production method according to claim 15, wherein the sulfate comprises lithium sulfate, sodium sulfate, potassium sulfate, calcium sulfate, magnesium sulfate, or any combination thereof.

17. The production method according to claim 16, wherein the sulfate comprises sodium sulfate, lithium sulfate, or a combination thereof.

18. The production method according to claim 1, wherein the neutral inorganic salt comprises an anhydride, a hydrate, or a mixture thereof.

19. The production method according to claim 1, wherein the neutral inorganic salt is present in an amount of 0.1 to 500 mol % based on amount of the organic compound.

20. The production method according to claim 1, wherein the neutral inorganic salt is present in an amount of 1 to 50 mol % based on amount of the organic compound.

* * * * *